US006428494B1

United States Patent
Schwenn et al.

(10) Patent No.: US 6,428,494 B1
(45) Date of Patent: Aug. 6, 2002

(54) CRANIAL ORTHOSIS WITH SAFETY STOP AND METHOD

(75) Inventors: Shannon R. Schwenn, Deltona; Alan T. Sandifer, Winter Springs, both of FL (US); Joseph W. Price, Newport Beach, CA (US)

(73) Assignee: Orthomerica Products, Inc., Newport Beach, CA (US)

( * ) Notice: Subject to any disclaimer, the term of this patent is extended or adjusted under 35 U.S.C. 154(b) by 0 days.

(21) Appl. No.: 09/535,884

(22) Filed: Mar. 28, 2000

(51) Int. Cl.[7] .................................................. A61F 5/00
(52) U.S. Cl. ............................................. 602/17; 2/414
(58) Field of Search ............................... 602/17; 2/410, 2/414, 417, 425, 209.1; 128/845, 846, 857; 224/151

(56) References Cited

U.S. PATENT DOCUMENTS

| | | |
|---|---|---|
| 678,417 A | 7/1901 | Muller |
| 2,825,328 A | 3/1958 | Olson |
| 2,855,202 A | 10/1958 | Klinne |
| 3,171,133 A * | 3/1965 | Steffen |
| 3,645,259 A | 2/1972 | Schulman |
| 3,834,379 A | 9/1974 | Grant |
| 4,352,352 A | 10/1982 | Janovsky et al. |
| 4,645,198 A | 2/1987 | Levenston |
| 4,646,728 A | 3/1987 | Takeda |
| 4,735,196 A | 4/1988 | Krag et al. |
| 4,776,324 A | 10/1988 | Clarren |
| 4,809,690 A | 3/1989 | Bouyssi et al. |
| 4,854,306 A | 8/1989 | Pujals, Jr. |
| 4,954,815 A | 9/1990 | Delmonte |
| 4,982,451 A | 1/1991 | Graham |
| 4,986,282 A | 1/1991 | Stackhouse et al. |
| 5,003,968 A | 4/1991 | Mars |
| 5,010,898 A | 4/1991 | de Kanawati et al. |
| 5,094,229 A | 3/1992 | Pomatto et al. |
| 5,308,312 A | 5/1994 | Pomatto et al. |
| 5,951,503 A | 9/1999 | Pomatto |

FOREIGN PATENT DOCUMENTS

| | | | |
|---|---|---|---|
| EP | 280042 | 8/1988 | |
| GB | 9114 | 9/1914 | |
| GB | 2082045 A * | 7/1981 | .......................... 1/4 |
| JP | 09201268 * | 1/1996 | ..................... 25/10 |
| JP | 01604220 * | 6/2000 | ........................... 3/4 |

OTHER PUBLICATIONS

Section 207: Is Your Class III Designation Really Final? H. Neal Dunning et al, Jan. 1999.
Diagnosis and Management of the Misshapen Head in the Neonate, S. David Moss, MD. et al, Pediatric Review, vol. 4/ Spring 1993.
Doc Band Information, 25 Pages, Jul./1996.
"Helmet treatments for plagiocephaly and congenital muscular torticollis," by S.K. Clarren et al., Journal of Pediatrics No. 14, No. 1, Jan. 1979.

* cited by examiner

*Primary Examiner*—Michael A. Brown
*Assistant Examiner*—Lalita M Hamilton
(74) *Attorney, Agent, or Firm*—Price and Gess

(57) ABSTRACT

A cranial orthosis includes a helmet member that can be expanded for mounting on a patient's head and subsequently contracted to be operatively positioned to permit the interior surface to reconfigure the patient's head to the desired shape is provided. The helmet member can have a split with a safety stop unit positioned on the helmet member to provide a safety limit to the adjustment against the patient's head. A safety stop unit can include a bellows member, a stop unit mounted on a flange extending from the helmet and a stop unit including a plurality of nestling components that can relatively move to permit the expansion step while nestling to a fixed position in a stacked configuration to provide a stop position against further closure of the cranial orthosis to protect the patient.

19 Claims, 3 Drawing Sheets

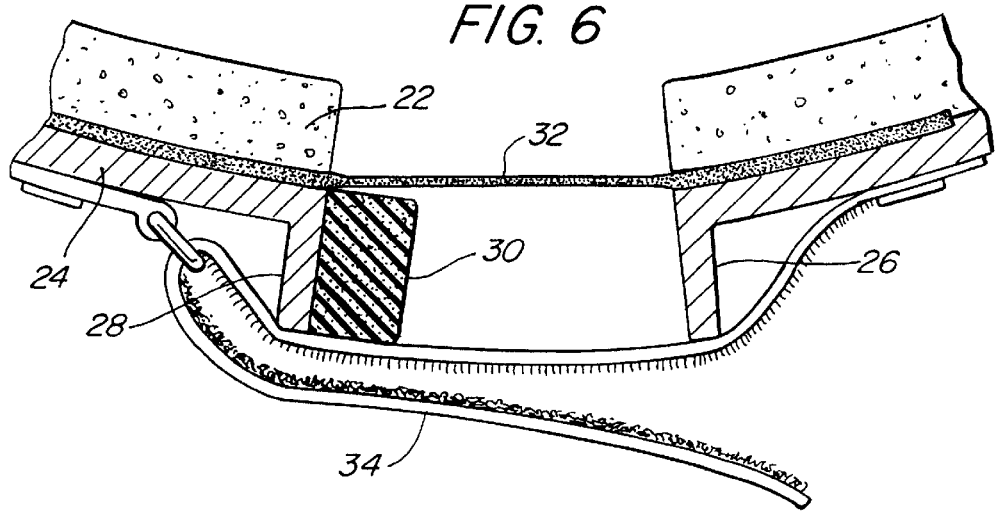
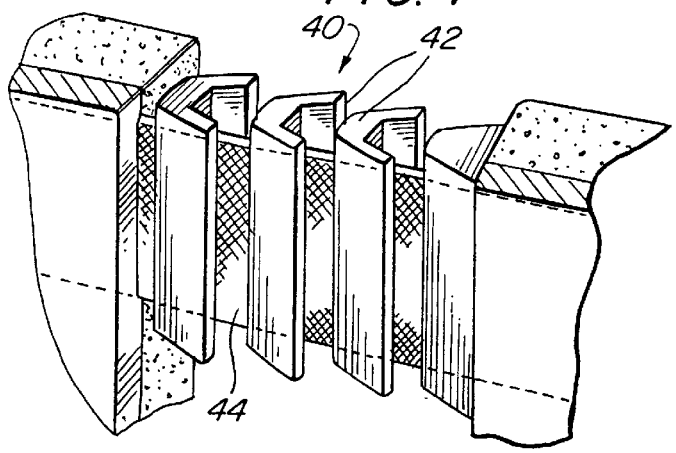
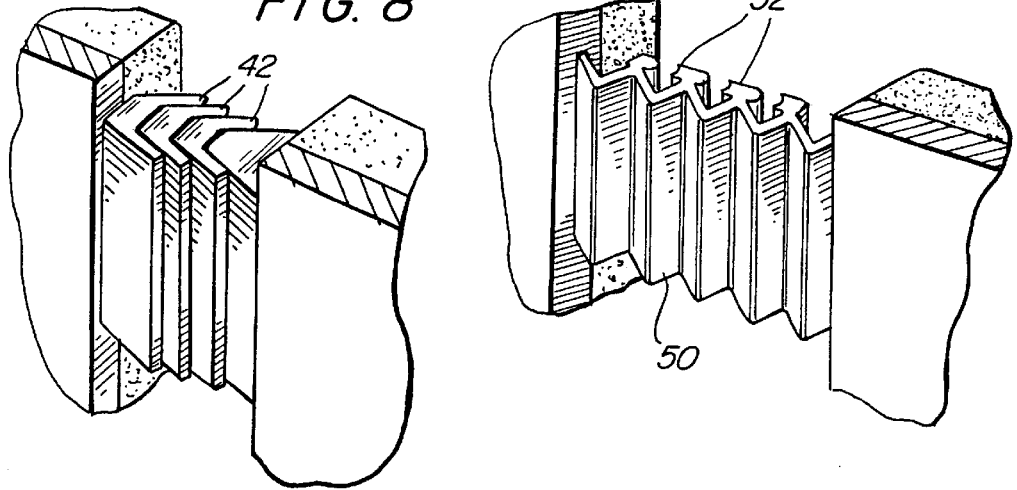

CRANIAL ORTHOSIS WITH SAFETY STOP AND METHOD

BACKGROUND OF THE INVENTION

1. Field of the Invention

The present invention is directed to a cranial orthosis to treat abnormal head shape in infants such as positional and/or deformational plagiocephaly and more particularly for providing a cranial orthosis with a safety feature and a method of application.

2. Description of Prior Art

Abnormal head shape in infants can result from a number of factors including inutero constraint, torticollis, sleeping position or any combination of these influences. In recent years, a documented increase in deformational plagiocephaly has been observed as a result of a change in the recommended sleeping position of the child to a supine sleeping position in an effort to reduce the risk of Sudden Infant Death Syndrome (SIDS).

The options available for the treatment of deformational plagiocephaly can include cranial vault remodeling surgery wherein the bones of the infant's calvarium are removed under general anesthesia, reshaped and replaced. This surgical procedure obviously encompasses all the risks commonly associated with major surgery. Specialists in this field including pediatricians, craniofacial surgeons and pediatric neurosurgeons have generally recognized that deformational plagiocephaly is a result of an extrinsic molding force and that surgery should only be resorted to as the last alternative. The preferred treatment option is orthotic cranioplasty in which a corrective orthosis is custom made for each patient. These orthoses apply mild pressure to the protruding areas of the deformity and leave room for growth in those areas that were flattened during the original deformation. The pressure applied should be limited to prevent skin breakdown or other harm to the infant. The effect of this orthotic cranioplasty in treating deformational plagiocephaly has been documented in the Journal of pediatrics, January 1979, page 499 in an article entitled, "Helmet Treatment for Plagiocephaly and Congenital Muscular Torticollis" by Clarren, et al. Reference can also be made to a subsequent U.S. Pat. No. 4,776,324 by one of the authors.

Generally, the treatment period can average 4 to 5 months and may even require a series of cranial orthoses to provide the desired shape. During this time period, the infant patient is basically being administered by his/her primary care provider, e.g., parent or parents that are not trained orthotists. The cranial orthosis is frequently removed and re-applied during this time period and the infant patient can not provide comment on any excessive application of pressure by the cranial orthosis.

There is still a desire in the orthopaedic industry to provide improvements and safety features in cranial orthosis.

SUMMARY OF THE INVENTION

A cranial orthosis includes a corrective head contact member mounted for example in a helmet member for mounting on a patient's head. The helmet member is configured for adjustment to permit an initial mounting and a subsequent application of confining pressure against selective areas of the head and voids to permit corrective growth. An interior surface of the helmet has been configured to provide a desired post treatment shape for the patient's head and a safety stop unit is positioned on the helmet member to provide a safety limit to any application of excessive pressure against the patient's head. The helmet member can be open on top or can extend about the entire patient's head or at least about the treatment area with a flexible member forming a portion of the helmet member. A strap member can be used for biasing the helmet member to an operative position to provide the desired treatment to the patient's head with the strap member anchored to the helmet member so that it can be tightened to maintain an operative position of the helmet member. An outer shell of the helmet member can be further split vertically along one side from top to bottom and a stop unit can be positioned to limit any closing movement of the edges of the helmet member on either side of the split opening. The stop unit can be formed as a bellows or diaphragm that can expand and contract and when contracted provides a stop position against any further closure of the helmet member on the patient's head. Other forms of the stop unit can be provided, such as a series of non-compressible spacers that are aligned on a resilient flexible band to limit contraction of the helmet while permitting expansion for insertion on the patient's head. Additionally, a stop unit can be positioned on a flange with a flexible resilient member positioned at a location inward from the stop unit. The stop unit may be positioned to define a secure contraction position of the helmet member to provide a positive alignment position for an untrained care provider.

The method of the present invention includes expanding the cranial orthosis for insertion about the treatment area of the patient's head and contracting the cranial orthosis to secure it on the patient's head within the limits of a safety stop member position.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 6 is a partial plan cross-sectional view of the second embodiment in a closed position;

FIG. 7 is a schematic view of an open position of a third embodiment of the present invention;

FIG. 8 is a schematic view of a closed position of a third embodiment of the present invention; and FIG. 9 is a partial prospective open view of a fourth embodiment of the present invention.

DETAILED DESCRIPTION OF THE PREFERRED EMBODIMENTS

Figure 1:
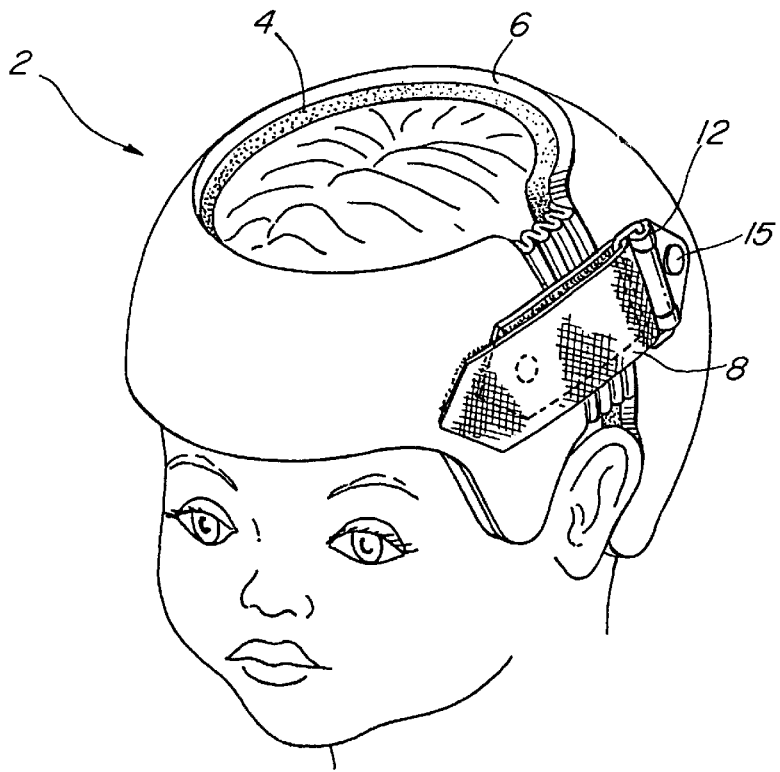
FIG. 1 is a side perspective view of a first embodiment of the present invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide safety features to protect the infant patient who is treated by non-professional care providers.

The cranial orthosis of the present invention is a non-invasive device that operates solely through the use of selected contact pressure created by wearing a customized orthosis. Generally, patients are fitted with an orthosis by a clinician specifically trained in the use of such devices. The orthosis comes into contact with intact skin and uses materials that are known in this industry to be safe and biocompatible. Generally, the treating clinician will take a negative plaster mold of an infant's head. A technician will then fill that mold with plaster and remove the negative mold to reveal a rough positive mold. An orthotist can modify the positive mold by reducing asymmetries while smoothing the mold surface and marking the mold to show trim lines. The positive mold can then be used for manufacturing a customized cranial orthosis. Alternatively, as known in the orthopaedic field, the head can be scanned with a video camera or a laser scan to determine the topography of the patient's head. Using these dimensional measurements, a positive mold can be initially formed with a multi-axis router and then subsequently finished by grinding to provide the desired mold to confine cranial growth in desired areas while providing voids to encourage growth in other areas.

In a preferred embodiment, the positive mold can be used for thermal forming by connecting the mold to a vacuum source and applying a fabric over the mold to enhance air flow. A layer of foam is applied to the mold by heating a sheet of approximately ½ inch ethylene foam and forming it directly over the mold. The foam can be formed in two halves for interior and posterior sections, trimmed, and the two halves can be glued together to create a single layer of foam with a seam over one ear. A sheet of approximately 3/16 inch co-polymer polypropylene can be heated to a thermal forming temperature. The plastic sheet is placed over the mold so that it is sealed and extends completely over the entire surface of the mold and is sealed around a vacuum pipe. When the vacuum is then applied, the plastic sheet is contracted to snuggly fit over the foam covered mold. The plastic is allowed to cool and then removed along with the foam from the mold by cutting. The resulting plastic foam shell is trimmed to the trim lines that are marked on the mold and the edges are buffed to a smooth shape. At the lateral opening over the ear, the foam is peeled away from the plastic and a safety stop member is positioned to close the lateral opening while permitting the cranial orthosis to be expanded for fitting on the patient's head with the safety stop unit limiting the potential contraction of the helmet.

A strap is riveted to the plastic shell on one side of the ear and a plastic chafe and metal loop is riveted to the plastic shell on the other side to provide an apparatus for securing the cranial orthosis to the infant patient's head.

Referring to FIG. 1, the cranial orthosis 2 or helmet of the present invention includes an inner polyethylene foam liner 4 that has been configured to a specific set of dimensions to provide a corrective orthosis to the patient's head. The exact dimension of the foam liner can vary but can be approximately ½ inch in thickness. An outer shell of a co-polymer polypropylene can be vacuum formed around the inner foam liner 4. The shell 6 can be formed from a sheet of approximately 3/16 inch in thickness. A flexible strap 8 can be anchored by a rivet 10 to the shell 6. The strap 8 can have a hook 9 and nap surface 11 structure such as Velcro™ to permit an adjustable fastening. A chafe buckle 12 can also be fastened by a rivet 15 to the helmet 2 to permit the strap 8 to extend through the buckle 12 for securing the helmet 2 on the head of the patient.

While the helmet 2 may have an application for children of various ages, it is believed that the prime application would be for children between the ages of 3 months to 18 months suffering from plagiocephalic, brachycephalic, post-surgical conditions (sagittal/coronal/lambdoid/metopic synostosis) bone deformations and syndrome infants (aperts/crouzons/pfiffer-post op). The principal head shapes that will be treated with this helmet is a plagiocephalic or parallelogram shape that experiences a flattening of the parietal/occipital area advancement of the insilateral ear and insilateral eye and flattening of the contralateral forehead. A brachycephalic condition is a flat and wide head which is manifested with an increased parietal width and decreased A-P length. Such a condition may be symmetrically flat or asymmetric and is usually present with increased posterior head height and reversed inclination of forehead. By utilization of the cranial orthosis, changes can be effected in the cranial vault and scull base. The average treatment time can be 4–5 months and it may be necessary to provide additional cranial orthosis of progressive differences in shape to improve cranial symmetry and/or shape. The helmet 2 will provide moderate pressure to prominent regions of the infant's cranium to limit further growth while providing voids in other areas to encourage growth. The split in the cranial orthosis 2 permits the orthosis to be opened or expanded for application to the patient's head. In the embodiments shown, the top of the cranial orthosis 2 is open, however, it can be closed depending on the specific treatment.

Figure 2:
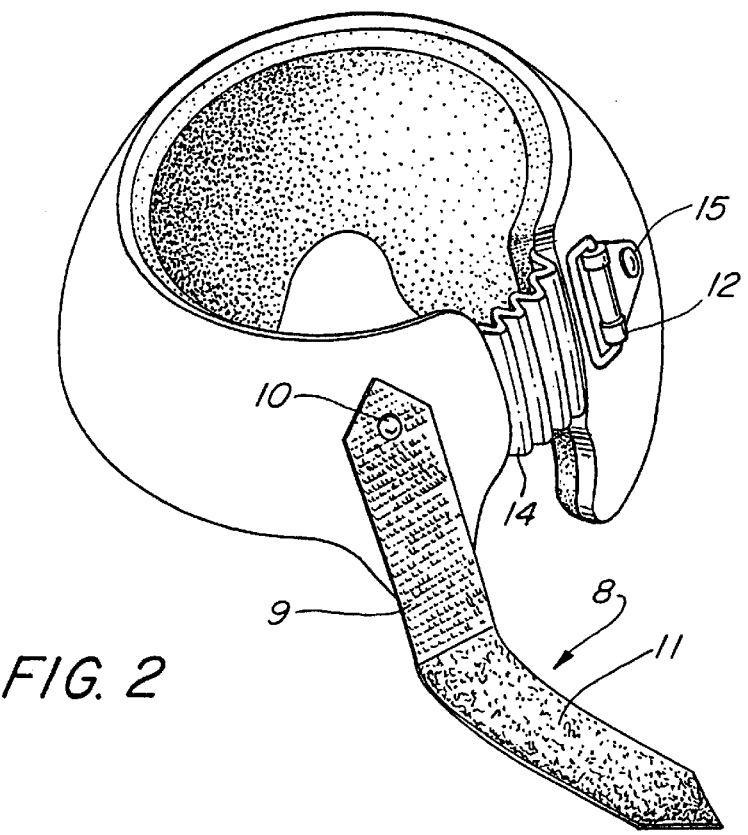
FIG. 2 is a perspective view of the first embodiment of the present invention.
Figure 3:
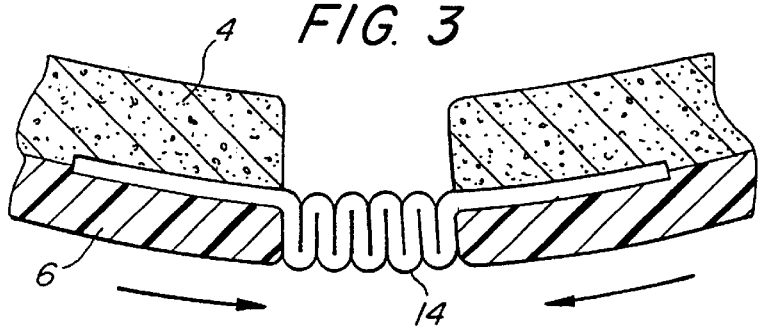
FIG. 3 is a partial cross-sectional view of the orthosis in a closed position.
Figure 4:
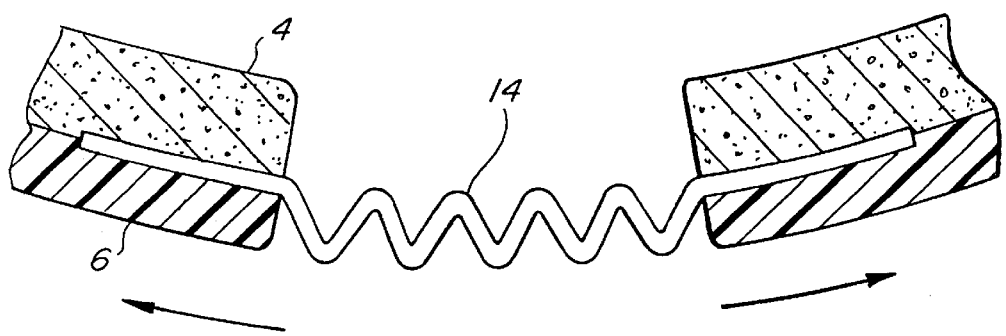
FIG. 4 is a partial cross-sectional view of the orthosis in an open position.

In FIGS. 1–4, a first embodiment of a safety member is provided for mounting in the split between the inner foam liner 4 and the outer shell 6 in order to provide a safety stop for limiting the closing of the helmet 2. As can be appreciated, a parent or primary care provider will frequently apply and take off the helmet 2 from the patient during the treatment period, for example, during bathing of the child. The strap 8 is primarily for the purpose of securing the helmet 2 on the patient's head as opposed to permitting a further contraction of the helmet 2 to provide progressively increasing pressure. The provision of a bellows member 14 for application as a safety stop is to facilitate the application of the helmet or orthosis 2 to the infant by a care provider who is frequently unskilled in this field. Thus, the bellows member 14 extends across the split opening between the outer shell 6 and as seen in FIG. 2, accommodates a spreading or expansion of the cranial orthosis 2 to facilitate mounting upon the patient's head. When mounted on the head, the bellows 14 contracts and assists in providing a safety stop to prevent excess pressure from being accidentally generated by the strap 8. The bellows member 14 is made from a plastic material that is sufficiently flexible to permit expansion but is stiff enough to limit contraction in a closed position as shown in FIG. 3. The bellows member 14 can have living hinges formed for the folds of the bellows member and can have the individual panel surfaces stiffened to provide a rigid configuration for providing a fixed position when the bellows member 14 is closed.

Figure 5:
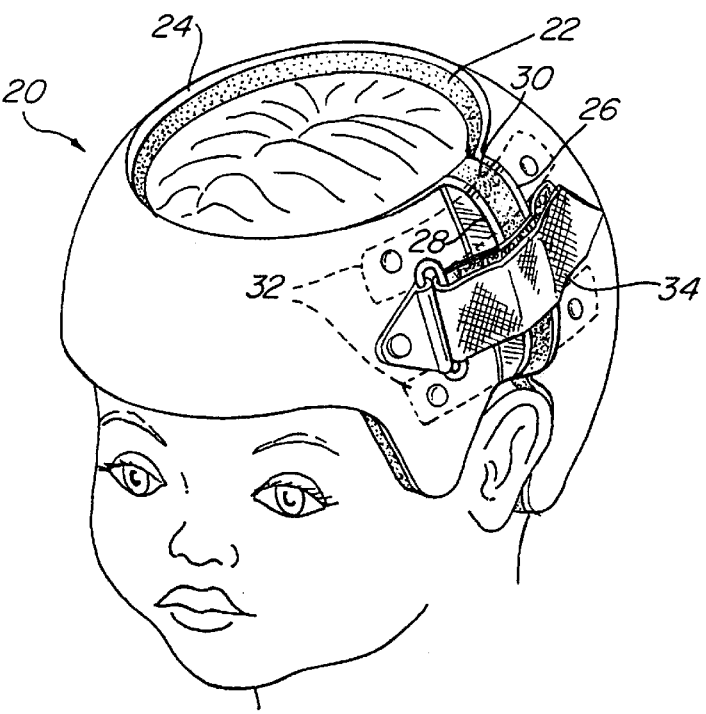
FIG. 5 is a perspective view of a second embodiment of the present invention in a closed position.

An alternative second embodiment of the invention is disclosed in FIG. 5 wherein a cranial orthosis 20 can be custom fitted in a similar manner as described above. The cranial orthosis 20 includes an inner foam liner 22 of the desired shape and an outer shell 24. The outer shell 24 has a pair of flanges 26 and 28. Mounted on flange 28 is a stop member 30 in the form of a block 30 to limit the contraction of the helmet 20. Also, extending across the split in the outer shell 24 is a resilient flexible band or bands 32 for biasing the helmet 20 to a contracted or closed position. As seen in FIG. 6, a strap 34 can be used to close the cranial orthosis 20 to a operative position with the stop member 30 preventing any excessive pressure being exerted on the patient's head as shown in FIG. 5. Thus, the care provider is assured that an effective treatment at a safe level is applied when the helmet 20 is closed against the stop member 30.

A third embodiment of the present invention is shown in FIGS. 7 and 8 wherein the split opening in the cranial orthosis is bridged by a composite stop member assembly 40 that has a plurality of non-compressible nestling spacer components 42 of roughly a U-shaped configuration that can be formed from molded plastic resin. These nestling components 42 can have a roughly cross-sectional U-shaped configuration with the arms of the "U" being of sufficient length to maintain an alignment to the nestling components 42 so that they stay in a stacked and potentially nestled configuration. The nestling components 42 can have a central vertical slot for receiving a resilient guide support member 44 which is anchored on either side of the split opening. As shown in FIG. 7, when the cranial orthosis is expanded for fitting on the patient's head, the resilient support member 44 stretches and the nestling components 42 can separate or slide to accommodate the expansion with a male projection member anchored at one side of the split open to receive an adjacent relatively movable female U-shaped component. Since the nestling components 42 have a substantially "U" configuration, they can self align and in effect close to provide a limit to the contraction of the cranial orthosis when a strap applies pressure. As an alternative embodiment, the stop member assembly, instead of being divided into a series of separate nestling components 42, can be a relatively movable single solid piece (not shown) that is mounted on the resilient support band extending between the sides of the split in the cranial orthosis. The resilient support band 44 has sufficient spring energy to remain in a state of tension during both expansion and contraction to insure a proper alignment with the rigid outer shell and to avoid contact with the patient's head.

A fourth alternative embodiment of the present invention is disclosed in FIG. 9 wherein a bellows 50 can be formed by plastic injection molding with living hinges on the bellows 50 and integrally molded nestling components 52 which are provided to permit not only expansion but a contracted closed safety stop position for contraction of the cranial orthosis.

As can be appreciated, other forms of a safety stop unit can be utilized to prevent excessive pressure from being applied by the strap to the cranial orthosis and accordingly to the patient's head and the preferred embodiments should not be considered limiting to the scope of the present invention.

The method of the present invention includes expanding a custom fitted cranial orthosis to permit insertion on an infant patient's head and subsequently contracting the cranial orthosis to secure it to the patient's head within the limits of a safety stop member position to thereby protect the child from accidental harm.

Those skilled in the art will appreciate that various adaptions and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A cranial orthosis for treatment of plagiocephaly and cogenital muscular torticollis comprising:
    a helmet member for mounting on a patient's head, the helmet member has a split opening to permit expansion for mounting and contraction for securing to the patient's head an interior surface of the helmet is configured to provide the desired shape for the patient's head by confining certain areas while permitting growth in other areas; and
    a stop unit positioned in the split opening on the helmet member to provide a safety limit for the contraction adjustment against the patient's head.

2. The cranial orthosis of claim 1, wherein the stop unit includes a flexible member forming a portion of the helmet member.

3. The cranial orthosis of claim 2, wherein the stop unit includes a bellows member that can expand and contract and when contracted provides a stop position against any further closure of the helmet member on the patient's head.

4. The cranial orthosis of claim 2, further including a member for biasing the helmet member to position to a contracted position on the patient's head.

5. The cranial orthosis of claim 4, wherein the member is a strap that is anchored to the helmet member and can be tightened to exert pressure on the helmet member.

6. The cranial orthosis of claim 2, wherein the helmet member is split from top to bottom along one side and has a pair of flanges extending radially outward along respective edges of the split, the stop unit is mounted on a flange to provide a pre-determined space between the respective flanges when they are moved to a closed position.

7. The cranial orthosis of claim 1, wherein the stop unit includes a resilient guide member extending across the split opening and mounts a stop member within the split opening.

8. The cranial orthosis of claim 1 wherein the stop unit includes a plurality of nestling components that can relatively expand and can contact each other to prevent further contraction of the split opening.

9. The cranial orthosis of claim 8 wherein the stop unit is a bellows member with integral nestling components.

10. The cranial orthosis of claim 8 wherein the stop unit includes a resilient guide member extending across the split opening and a plurality of nestling components that are relatively moveable and mounted on the resilient guide member and can contact each other to prevent a pre-determined contraction of the split opening.

11. The cranial orthosis of claim 1 wherein the nestling components have a U-shaped cross-section configuration.

12. The cranial orthosis of claim 11 further including a central aperture in the nestling components and a resilient guide support member secured on either side of the opening and supporting the nestling components by extending through the central aperture.

13. The cranial orthosis of claim 12 wherein the member holding the helmet member from expanding extends across the stop unit.

14. The cranial orthosis of claim 1 further including a resilient guide support member secured on either side of the opening and supporting the nestling components.

15. A method of applying a cranial orthosis for treatment of an infant's head comprising the steps of:
    expanding a split opening on the cranial orthosis to mount the cranial orthosis on the infant's head;

contracting the cranial orthosis about the infant's head until a stop unit positioned in the split opening prevents further contraction; and securing the cranial orthosis against further movement.

16. The method of claim 15 further including the steps of providing a stop member in the form of a bellows member as the stop unit and the step of expanding causes the bellows member to expand and the step of contracting causes the bellows member to contract to form a stop position against any further closure of the cranial orthosis.

17. The method of claim 15 further including the steps of providing a plurality of nestling components and the step of expanding permits the nestling components to move relative to the cranial orthosis and the step of contracting causes the nestling components to align in a stack and provide a stop position against any further closure of the cranial orthosis.

18. The method of claim 15 wherein the steps of securing includes securing a flexible strap member across a portion of the cranial orthosis supporting the stop unit to fasten the cranial orthosis on the infant's head.

19. A cranial orthosis for treatment of an infant's head comprising:

a helmet member for mounting on an infant's head, the helmet member has an opening adjacent an ear position when mounted to permit expansion for mounting and contraction for securing to the infant's head, an interior surface of the helmet is configured to provide the desired shape for the infant's head by confining certain areas while permitting growth in other areas;

a stop unit having a plurality of relatively movable nestling components mounted in the opening, the nestling components freely permitting an expansion of the helmet member for mounting on the infant's head, the nestling components are compressed together when the helmet member is contracted for application to the infant's head and provide a safety stop position when fully compressed within the opening to prevent further contraction against the infant's head; and a member to hold the helmet member from expanding to securely maintain the helmet member on the infant's head.

* * * * *